United States Patent
Chiarello et al.

(10) Patent No.: US 6,750,357 B1
(45) Date of Patent: Jun. 15, 2004

(54) RHODAMINE-BASED FLUOROPHORES USEFUL AS LABELING REAGENTS

(75) Inventors: Ronald H. Chiarello, Castro Valley, CA (US); Wing Liu, Belmont, CA (US); Kathy E. Yokobata, Sunnyvale, CA (US)

(73) Assignee: SynGen, Inc., San Carlos, CA (US)

( * ) Notice: Subject to any disclaimer, the term of this patent is extended or adjusted under 35 U.S.C. 154(b) by 0 days.

(21) Appl. No.: 09/344,226

(22) Filed: Jun. 25, 1999

(51) Int. Cl.$^7$ .............................................. C07D 311/78

(52) U.S. Cl. ........................ 549/394; 436/172; 436/800

(58) Field of Search ........................ 549/394; 436/172, 436/800

(56) References Cited

U.S. PATENT DOCUMENTS

| | | |
|---|---|---|
| 2,153,059 A | 4/1939 | Eckert et al. |
| 2,242,572 A | 5/1941 | Eckert et al. |
| 3,822,270 A | 7/1974 | Reynolds |
| 3,849,065 A | 11/1974 | Schmeidl |
| 3,932,415 A | 1/1976 | Reynolds |
| 4,005,092 A | 1/1977 | Reynolds |
| 4,290,955 A | 9/1981 | Cincotta et al. |
| 4,336,186 A | 6/1982 | Gargiulo et al. |
| 4,401,796 A | 8/1983 | Itakura |
| 4,415,732 A | 11/1983 | Caruthers et al. |
| 4,557,862 A | 12/1985 | Mangel et al. |
| 4,647,675 A | 3/1987 | Mayer et al. |
| 4,668,777 A | 5/1987 | Caruthers et al. |
| 4,683,195 A | 7/1987 | Mullis et al. |
| 4,683,202 A | 7/1987 | Mullis |
| 4,711,955 A | 12/1987 | Ward et al. |
| 4,828,979 A | 5/1989 | Klevan et al. |
| 4,868,105 A | 9/1989 | Urdea et al. |
| 4,900,686 A * | 2/1990 | Arnost et al. |
| 4,965,349 A | 10/1990 | Woo et al. |
| 5,047,519 A | 9/1991 | Hobbs, Jr. et al. |
| 5,175,269 A | 12/1992 | Stavrianopoulos |
| 5,210,015 A | 5/1993 | Gelfand et al. |
| 5,231,191 A | 7/1993 | Woo et al. |
| 5,241,060 A | 8/1993 | Engelhardt et al. |
| 5,328,824 A | 7/1994 | Ward et al. |
| 5,371,241 A | 12/1994 | Brush |
| 5,442,045 A | 8/1995 | Haugland et al. |
| 5,449,767 A | 9/1995 | Ward et al. |
| 5,476,928 A | 12/1995 | Ward et al. |
| 5,489,678 A | 2/1996 | Fodor et al. |
| 5,698,411 A | 12/1997 | Lucas et al. |
| 5,733,719 A | 3/1998 | Jaffe et al. |
| 5,776,720 A | 7/1998 | Jaffe et al. |
| 5,846,737 A * | 12/1998 | Kang |

FOREIGN PATENT DOCUMENTS

| | | |
|---|---|---|
| EP | 0252683 | 1/1988 |
| EP | 0251786 | 11/1994 |
| WO | 96/36729 | 11/1996 |

OTHER PUBLICATIONS

Bauman et al., "A New Method for Fluorescence Microscopical Localization of Specific DNA Sequences by in situ Hybridization of Fluorochrome–labelled RNA," *Exp. Cell Res., 128*, pp. 485–490, 1980.

Belkum and Niesters, "Nucleic Acid Amplification and Related Techniques in Microbiligical Diagnostics and Epidemiology," *Cell. Mol. Biol., 41* (5), pp. 615–623, 1995.

Guatelli et al., "Isothermal, in vitro Amplification of Nucleic Acids by a Multienzyme Reaction Modeled after Retroviral Replication," *Proc. Natl. Acad. Sci. USA, 87*, pp. 1874–1878, 1990.

Haugland, Richard P., "Long–wavelength Dyes," Chapter 1, Section 1.6 in *Handbook of Fluorescent Probes and Research Chemicals, 6$^{th}$* Edition, pp. 29–35, 1996.

Haugland, Richard P., "Chemically Modified Nucleotides, Oligonucleotides and Nucleic Acids," Chapter 8, Section 8.2 in *Handbook of Fluorescent Probes and Research Chemicals, 6$^{th}$* Edition, pp. 157–161, 1996.

Haughland, Richard P., part of "Enzymes, Enzyme Substates and Enzyme Inhibitors," Chapter 10 in *Handbook of Fluorescent Probes and Research Chemicals, 6$^{th}$* Edition, pp. 201–229, 1996.

Heid et al., "Real Time Quantitative PCR," *Genome Research, 6*, pp. 986–994, 1996.

Holland et al., "Detection of Specific Polymerase Chain Reaction Product by Utilizing the 5'→3'Exonuclease Activity of *Thermus aquaticus* DNA Polymerase," *Proc. Natl. Acad. Sci. USA, 88*, pp. 7276–7280, 1991.

Hung et al., "Comparison of Fluorescence Energy Transfer Primers with Different Donor–acceptor Dye Combinations," *Analytical Biochemistry, 255*, pp. 32–38, 1998.

Hung et al., "Energy Transfer Primers with 5– or 6–Carboxyrhodamine–6G as Acceptor Chromophores," *Analytical Biochemistry, 238*, pp. 165–170, 1996.

Ioffe and Otten, "Studies in the Field of Rhodamine Dyes and Compounds Related to Them: XII. Diacetyl Derivatives of Rhodamine and Rhodol; The Structure of the Colorless Forms of Fluorane Dyes," trans. from *Zhurnal Organicheskoi Khimmii, 1* (2), pp. 336–339, Feb. 1965, in *Journal of Organic Chemistry of the* USSR, 1 (2), pp. 326–329, Feb. 1965.

(List continued on next page.)

*Primary Examiner*—Taofiq Solola
(74) *Attorney, Agent, or Firm*—Medlen & Carroll, LLP (57) ABSTRACT

Fluorescent dyes based on rhodamine are derivatized to form labeled conjugates that fluoresce upon excitation with light of an appropriate wavelength. Particularly preferred embodiments are certain single isomer form rhodamine phosphoramidites. These rhodamine phosphoramidites enhance the efficiency of synthesizing rhodamine-labeled oligonucleotides by solid phase methods. Conjugate embodiments of the invention are prevented from being converted to a non-fluorescent lactam form due to having a fully substituted amide linkage derived from the 3-position carboxylate.

11 Claims, 1 Drawing Sheet

OTHER PUBLICATIONS

Ioffe and Otten, "Studies in the Field of Rhodamine Dyes and Compounds Related to Them: XIII. The Structure of the Colored Forms of Rhodamine and Rhodol," transl. from *Zhurnal Organicheskoi Khimmii, 1* (2), pp. 340–343, Feb. 1965, in *Journal of Organic Chemistry of the USSR, 1* (2), pp. 330–332, Feb. 1965.

Ioffe and Otten, "Studies in the Field of Rhodamine Dyes and Compounds Related to Them: XIV. Interconversion of the Colorless and Colored Forms of Rhodamine and Rhodol," translated fom *Zhurnal Organicheskoi Khimmii, 1* (2), pp. 343–346, Feb. 1965, in *Journal of Organic Chemistry of the USSR, 1* (2) pp. 333–336, Feb. 1965.

Köster et al., "N–Acyl Protecting Groups for Deoxynucleosides: A Quantitative and Comparative Study," *Tetrahedron, 37,* pp. 363–369, 1981.

Lawrence et al., "Sensitive, High–Resolution Chromatin and Chromosome Mapping In Situ. Presence and Orientation of Two Closely Integrated Copies of EBV in a Lymphoma Line," *Cell 52,* pp. 51–61, 1988.

Lee et al., "DNA Sequencing with Dye–labeled Terminators and T7 DNA Polymerase Effects of Dyes and dNTPs on Incorporation of Dye–terminators and Probability Analysis of Termination Fragments," *Nucleic Acids Research, 20* (10), pp. 2471–2483, 1992.

Livak et al, "Oligonucleotides with Fluorescent Dyes at Opposite Ends Provide a Quenched Probe System Useful for Detecting PCR Product and Nucleic Acid Hybridization," *PCR Methods and Applications, 4,* pp. 357–362, 1995.

Morré et al., "RNA Amplification by Nucleic Acid Sequence–based Amplification with an Internal Standard Enables Reliable Detection of *Chlamydia trachomatis* in Cervical Scrapings and Urine Samples," *J. Clin. Microbiol., 34,* (12), pp. 3108–3114, 1996.

Mullah and Andrus, "Automated Synthesis of Double Dye–labeled Oligonucleotides using Tetramethyl–rhodamine (TAMRA) Solid Supports," *Tetrahedron Letters, 38* (33), pp. 5751–5754, 1997.

Murakami et al., "Fluorescent–labeled Oligonucleotide Probes: Detection of Hybrid Formation in Solution by Fluorescence Polarization Spectroscopy," *Nucleic Acids Research, 19* (15), pp. 4097–4102, 1991.

Nazarenko et al., "A Closed Tube Format for Amplification and Detection of DNA Based on Energy Transfer," *Nucleic Acids Research 25* (12), pp. 2516–2521, 1997.

Pinkel et al., "Fluorescence in situ Hybridization with Human Chromosome–specific Libraries: Detection of Trisomy 21 and Translocations of Chromosome 4," *Proc. Natl. Acad. Sci. USA, 85,* pp. 9138–9142, 1988.

Rudkin and Stollar, "High Resolution Detection of DNA–RNA Hybrids in situ by Indirect Immuno–fluorescence," *Nature 265,* pp. 472–473, 1977.

Sanger et al., Cloning in Single–Stranded Bacteriophage as an Acid to Rapid DNA Sequencing, *J. Mol. Biol., 143,* pp. 161–178, 1980.

Schreier and Cortese, "A Fast and Simple Method for Sequencing DNA Cloned in the Single–stranded Bacteriophage M13," *J. Mol. Biol., 129,* pp. 169–172, 1979.

Schulhof et al., "The Final Deprotection Step in Oligonucleotide Synthesis is Reduced to a Mild and Rapid Ammonia, Treatment by Using Labile Base–protecting Groups," *Nucleic Acids Research, 15* (2), pp. 397–416, 1987.

Smith et al., "Fluorescence Detection in Automated DNA Sequence Analysis," *Nature, 321,* pp. 674–679, 1986.

Smith et al., "The Synthesis of Oligonucleotides Containing an Aliphatic Amino Group at the 5' Terminus: Synthesis of Fluorescent DNA Primers for Use in DNA Sequence Analysis," *Nucleic Acids Research, 13* (7), pp. 2399–2412, 1985.

Theisen et al., "Fluorescent Dye Phosphoramidite Labelling of Oligonucleotides," *Nucleic Acids Symposium Seies, 27,* pp. 99–100, 1992.

Theisen et al., "Fluorescent Dye Phosphoramidite Labelling of Oligonucleotides," *Tetrahedron Letters, 33* (35), pp. 5033–5036, 1992.

Tyagi and Kramer, "Molecular Beacons: Probes that Fluoresce Upon Hybridization," *Nature Biotechnology, 14,* pp. 303–308, 1996.

Tyagi et al., "Multicolor Molecular Beacons for Allele Discrimination," *Nature Biotechnology, 16,* pp. 49–53, 1998.

Walker et al., "Isothermal in vitro Amplification of DNA by a Restriction Enzyme/DNA Polymerase System," *Proc. Natl. Acad. Sci. USA, 89,* pp. 392–396, 1992.

Walker et al., "Strand Displacement Amplification—an Isothermal, in vitro, DNA Amplification Technique," *Nucleic Acids Research, 20* (7), pp. 1691–1696, 1992.

Yu et al., "Cyanine Dye dUTP Analogs for Enzymatic Labelling of DNA Probes," *Nucleic Acids Research, 22* (15), pp. 3226–3232, 1994.

Langer et al., "Enzymatic Synthesis of Biotin–labeled Polynucleotides; Novel Nucleic Acid Affinity Probes," *Proc. Natl. Acad. Sci. USA, 78* (11), pp. 6633–6637, 1981.

Acrōs Organics, product list and information on Rhodamine–based compound, *1995–1996 Catalog,* pp. 1513–1515.

Amersham Pharmacia Biotech, "Fluorescent Nucleotides," *Catalogue '98,* p. 127, 1997/1998.

Boehringer Mannheim, "Nucleotides for Non–radioactive Labeling," *1997 Biochemicals Catalog,* pp. 90–93, 1997.

The Society of Dyers and Colourists, entries re xanthenes as relates to rhodamines and rhodols, *Colour Index, 3rd* Edition, pp. 64 and 4419–4430, 1971.

Life Technologies, *GIBCO BRL Products & Reference Guide,* pp. 17–2 through 17–5, 1997/1998.

PE Biosystems, "User Bulletin: ABI 392/4 Nucleic Acid Synthesizers," re Synthesis and Purification of Fluorescently Labeled Oligonucleotides Using Dye Phosphoramidites (User Bulletin No. 78), WorldWide Web site at http://www2.perkin–elmer.com/ab/techsupp/doclib/nasynth/multi/ub/html/UB78.html, 8 pages, 1998.

PE Biosystems, "DNA Synthesis FAQs" (Frequently Asked Questions), World Wide Web site at http://www2perkin–elmer.com/ab/techsupp/dnasynfaq.html, 9 pages, 1998.

Peninsula Laboratories, Inc., Product information on "5' Labeling Products," (Cat. No. N4345), 1992.

Peninsula Laboratories, Inc., Product information on "3' Labeling Products," (Cat. No. N4340), 1991.

Peninsula Laboratories, Inc., Product information on "Modified Thymidine Labeling Products," (Cat. No. N4082), 1994.

Glen Research, "Rhodamine Labelling," from 1998 Catalog (Products for DNA Research), p. 39, 1998.

"New Fluorescent Reagents—TAMRA–dT, DABCYL–dT," *The Glen Report* (company bulletin of Glen Research), 11 (1), p. 5, Jul. 1998.

Venkataraman, K., "Chapter XXIV: Xanthene and Acridine Dyes," *The Chemistry of Synthetic Dyes, 2,* Academic Press, NY, pp. 740–760, 1952.

* cited by examiner

RHODAMINE-BASED FLUOROPHORES USEFUL AS LABELING REAGENTS

FIELD OF THE INVENTION

The invention generally relates to methods of labeling organic compounds for fluorescent detection. More particularly, the invention relates to rhodamine-based fluorophores which are made useful by derivatization with organic molecules, and have application so as to label biomolecules such as synthetic oligonucleotides and proteins. The fluorophores are single isomers, are stable and reactive in standard phosphite chemistry, and the conjugates remain fluorescent.

BACKGROUND OF THE INVENTION

The use of fluorescent dyes as detection labels has found widespread application in molecular biology, cell biology and molecular genetics. In particular, the use of fluorescently labeled oligonucleotides has expanded with advancements in DNA sequencing, fluorescence in situ hybridization (FISH), hybridization assays including nucleic acid arrays ("DNA chips"), probe capture assays, fluorescence polarization studies, and DNA amplification assays: polymerase chain reaction (PCR), isothermal amplification assays (strand displacement amplification (SDA), nucleic acid sequence based amplification (NASBA), self-sustained sequence replication (3SR), and with fluorescent primer and/or probe detection ("Taqman" assay).

Current automated DNA sequencing methods make use of multiple fluorescent labels for concurrent detection of base sequence in a single gel lane or capillary. Most of the commonly used fluorescent dyes for sequencing are produced as a mixture of isomers, including those of the rhodamine family. (In reference to rhodamine dyes, we will use the numbering scheme described in the *Colour Index* by the Association of Textile Chemists, 2nd Edition, 1971.) Single isomer dye labels are preferred for high resolution techniques such as DNA sequencing and capillary electrophoresis, because slight differences in spectral properties exist between different isomeric forms of the fluorophores. In addition, differences in the electrophoretic mobilities of 5- and 6-isomer fluorophore-tagged primers (e.g. 5- and 6-carboxytetramethylrhodamine) can lead to band broadening if mixtures of isomers are used (Hung et al., *Analytical Biochem.*, 238, 165–170, 1996). Therefore, single isomer forms must be purified before preparing fluorescent dye labeling reagents intended for use in labeling oligonucleotides for DNA sequencing.

Some fluorescent dye labels can be attached to the 5' end of oligonucleotides during the process of synthesizing the primers (e.g. fluorescein using a fluorescein phosphoramidite reagent). These dye phosphoramidites react properly under phosphite chemistry conditions because protection of the two active oxygen groups on the fluorescein moiety prevent possible side reactions between the phosphoramidite and fluorescein. In addition, modification with the protecting groups holds the 3-position carboxylic acid function in the closed ring lactone form, preventing proton donation from the carboxylate to the N,N-diisopropylamino phosphoramidite. Protonation would convert the diisopropylamino moiety into a good leaving group, which could decompose the reagent. Some rhodamine phosphoramidites synthesized (for example, U.S. Pat. No. 5,231,191, issued Jul. 27, 1993, inventors Woo et al.) have the 3-position carboxylic acid function existing in equilibrium between the closed (lactone) and open (acid) form. When the reagent is used in oligonucleotide synthesis, the "acidic" environment will favor formation of the carboxylate-onium cation form. Proton donation from the carboxylic acid moiety to the N,N-diisopropylamino phosphoramidite could occur and result in reagent instability, compromising oligonucleotide labeling efficiency.

Some fluorescent dye labels (e.g. fluorescein and related derivatives) retain their fluorescent properties during cleavage of the labeled oligonucleotide from the solid phase support and removal of protecting groups with concentrated aqueous ammonia, the standard method in current practice. However, dyes in the rhodamine family are susceptible to chemical modification by the ammonia treatment, which drastically decreases their fluorescent properties. Thus, it is a general practice for rhodamine-type dyes to be attached to the 5' end of oligonucleotides which have been modified with linker functionalities (e.g. primary amine) after automated synthesis, cleavage and deprotection. This dye labeling requires additional steps and manual labor, incurring greater cost and inconvenience in the overall synthesis of 5'-rhodamine dye-labeled oligonucleotides.

SUMMARY OF THE INVENTION

In one aspect of the present invention, fluorogenic compounds and compositions are provided that are based upon rhodamine. In rhodamine there is a 3-position carboxylate. Fluorogenic compounds of this invention, or fluorophores, have the 3-position carboxylate converted to a fully substituted amide. One substituent of the amide nitrogen is a group that is effective to block lactam ring formation. The other substituent of the amide nitrogen is useful in making, or includes, desired derivatives. Useful derivatives of these fluorophores can be made for labeling organic compounds for fluorescent detection. Preferred organic compounds are biomolecules such as a peptide, protein, amino acid, nucleotide, oligonucleotide, or nucleic acid polymer. The conjugation is preferably via a phosphoramidite linkage when synthesizing labeled oligonucleotides, and may be by a variety of the known protein conjugation chemistries when synthesizing labeled peptides or labeling.

Formula A below illustrates a rhodamine-based, fluorophore moiety of this invention where $R_a$ and $R_{a'}$ are both non-hydrogen substituents for the amide nitrogen.

FORMULA A

In the Formula A structure, $R_1$ and $R_{10}$ taken alone are hydrogen or halogen; $R_2$, $R_5$, $R_6$ and $R_9$ taken alone are hydrogen, alkyl, carboxyalkyl, aminoalkyl, alkylether, alkylthioether, halogen or alkoxy; $R_3$, $R_4$, $R_7$ and $R_8$ taken alone are hydrogen, alkyl, carboxyalkyl, aminoalkyl, cycloalkyl, aryl, or alkyl, cycloalkyl, or aryl substituted so as to have additional functional groups attached, including but not limited to alkoxy, sulfate, phosphate, or nitrate; $R_2$ and $R_3$ taken together are alkyl chains each having from 2 to 5 carbon atoms connecting the 2' carbon to the nitrogen attached to the 3' carbon; $R_9$ and $R_8$ taken together are alkyl chains each having from 2 to 5 carbon atoms connecting the 7' carbon to the nitrogen attached to the 6' carbon; $R_4$ and $R_5$ taken together are alkyl, each having from 2 to 5 carbon atoms connecting the 4' carbon to the nitrogen attached to the 3' carbon; $R_6$ and $R_7$ taken together are alkyl, each having from 2 to 5 carbon atoms connecting the 5' carbon to the nitrogen attached to the 6' carbon; $R_3$ and $R_4$ taken together form an alkyl or alkylene chain containing up to 5 atoms in the principal chain, consisting of carbon and one or more heteroatoms from the group consisting of nitrogen or oxygen, with both terminal valence bonds of said chain being attached to the nitrogen attached to the 3' carbon; $R_7$ and $R_8$ taken together form an alkyl or alkylene chain containing up to 5 atoms in the principal chain, consisting of carbon and one or more heteroatoms from the group consisting of nitrogen or oxygen, with both terminal valence bonds of said chain being attached to the nitrogen attached to the 6' carbon; $R_{11}$, $R_{12}$, $R_{13}$, and $R_{14}$ are each hydrogen or halogen.

One function of the $R_{a'}$ substituent is to block lactam ring formation, and consequently it can be chosen from a wide variety of substituents such as alkyl, carboxyalkyl, aminoalkyl, cycloalkyl, aryl, or arylalkyl. The size of the substituent as a blocking group against lactam ring formation can vary considerably.

The linkage to desired conjugated substances is formed through the $R_{a'}$ substituent or derivatives of the $R_{a'}$ substituent. Typically one may select an $R_{a'}$ that is alkyl, carboxyalkyl, aminoalkyl, cycloalkyl, arylalkyl, but preferably $R_{a'}$ is chosen so as to include a chemically reactive functional group for further derivatization. Suitable functional groups are amines, alcohols, halogens, carboxylates, hydrazines, sulfhydryls, sulfates, phosphates, or nitrates. The $R_{a'}$ substituent in its simplest form with a chemically reactive functional group may be —$CH_2CH_2OH$ from which the hydroxyl may be used to prepare the desired various derivatives or conjugates.

Because compounds of the invention preferably possess functional groups linked through the 3-position carboxyl group the linkage converts the 3-position carboxylate to a non-acidic function (e.g. amide), which confers better stability to derivatives such as phosphoramidites. By virtue of doing the chemistry through the 3-position carboxyl group, the inventive dyes and labeling derivatives are single isomer forms, unlike compounds which require purification from mixtures of 5- and 6-position carboxyrhodamines before preparing oligonucleotide labeling reagents.

Since compounds of the invention possess a fully substituted amide nitrogen, the dyes are prevented from being converted to a non-fluorescent lactam form. Phosphoramidites and derivatized solid phase support matrix reagents of this invention allow efficient, fully automated synthesis of rhodamine labeled oligonucleotides.

DETAILED DESCRIPTION OF PREFERRED EMBODIMENTS

One aspect of the invention is to provide rhodamine-based dyes conjugated to organic molecules, more preferably to biomolecules. We believe that none of the compounds previously described in the chemical or biochemical literature possess functional groups linked through the 3-position carboxyl group of rhodamine to biomolecules such as oligonucleotides and proteins. The rhodamine-based dyes are more easily synthesized as single isomer derivatives, which are important when labeling oligonucleotides for DNA sequencing. By contrast, traditionally used carboxyrhodamines require purification of mixed isomers to single isomer forms before labeling derivatives can be synthesized. Further, the rhodamine-based compounds of this invention possess an amide linkage derived from the 3-position carboxylate, which converts the carboxylate group to a non-acidic function. This improves stability of phosphoramidites derived therefrom. Fully substituting the amide nitrogen prevents conversion of the dyes to a non-fluorescent lactam form.

Figure 1:
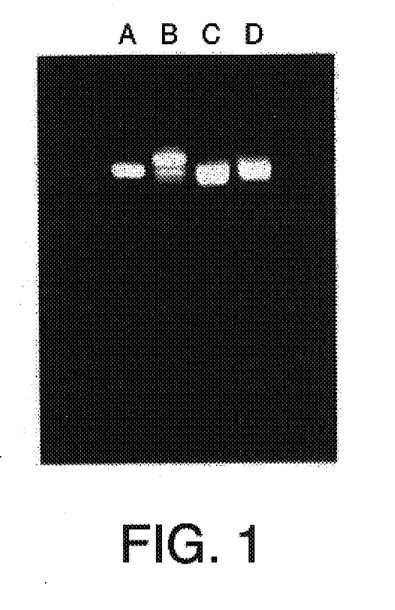
FIG. 1 illustrates a photograph of a polyacrylamide gel following electrophoresis in which the lanes contain oligonucleotides labeled in accordance with the invention. (Lane A was a poly-dT 9 mer, Lane B was a poly-dT 10 mer, Lane C was a poly-dT 11 mer, and Lane D was a poly-dT 11 mer, and Lanes A, C, and D were labeled at the 5'-end during synthesis whereas Lane B was labeled at the 3'-end during synthesis); and, FIG. 2 illustrates a photograph of a polyacrylamide gel following electrophoresis of fluorescent rhodamine-labeled protein in accordance with the invention.
Figure 2:
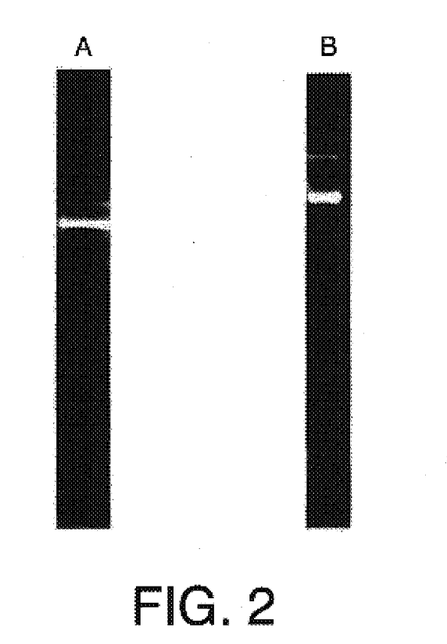

FIGS. 1 and 2 illustrate labeling uses of six embodiments of this invention (Compounds 4–9), the preparations of which are exemplified by Examples 4–10 described hereinafter.

Turning briefly to FIG. 1, rhodamine-labeled oligonucleotides were electrophoresed in a 19% polyacrylamide, 10 M urea, 89 mM Tris-borate, 2 mM ethylenediaminetetraacetic acid (EDTA) (TBE buffer) gel using standard conditions for gel purification of oligonucleotides (Sambrook et al., *Molecular Cloning: A Laboratory Manual*, 2$^{nd}$ Edition, Cold Spring Harbor Laboratory Press, 1989). The gel was illuminated on an ultraviolet light box and fluorescent images were captured using a NucleoVision CCD camera system fitted with a rhodamine filter (NucleoTech, Inc., Foster City, Calif.). Lane A contained poly-dT 9 mer labeled at the 5' end during synthesis using the rhodamine-based embodiment designated Compound 5. Lane B contained poly-dT 10 mer labeled at the 3' end during synthesis using the rhodamine-based embodiment Compound 7. Lane C contained poly-dT 11 mer labeled at the 5' end during synthesis using Compound 4. Lane D contained poly-dT 11 mer labeled at the 5' end during synthesis using Compound 6.

Turning briefly to FIG. 2, bovine serum album protein was conjugated with the indicated labeling reagent and electrophoresed in a sodium dodecyl sulfate (SDS)-polyacrylamide gel (15% polyacrylamide with 5% stacking gel, 25 mM Tris, 250 mM glycine, 0.1% SDS buffer) under standard conditions (Sambrook et al., *Molecular Cloning: A Laboratory Manual*, 2$^{nd}$ Edition, Cold Spring Harbor Laboratory Press, 1989). The gel was illuminated on an ultraviolet light box and fluorescent images were captured using a NucleoVision CCD camera system fitted with a rhodamine filter (NucleoTech, Inc., Foster City, Calif.). Lane A shows bovine serum albumin conjugated with Compound 8. Lane B shows bovine serum albumin conjugated with Compound 9.

As illustrated by FIG. 1, dye-derivatized solid support matrices of the invention allow automated synthesis of 3' end labeled oligonucleotides; dye phosphoramidites allow 5' end labeling during synthesis of oligonucleotides. Further, the subject invention can be practiced so as to add a dye-labeled dU residue to an oligonucleotide at any point within the sequence during automated oligosynthesis.

The fluorescence excitation and emission properties of the rhodamine dyes used in practicing this invention are similar to rhodamines used in commercially available automated fluorescent DNA sequencing and fluorescent assay detection instrumentation, with improved spectral separation from commonly used fluorescein derivatives. The inventive derivatives and conjugates retain their ability to fluorescence upon excitation with light of a determinable wavelength. In general, the derivatives and conjugates of this invention are excitable with light at a wavelength of 500 to 700 nm and fluoresce at a wavelength of 520 to 750 nm.

As illustrated by FIG. 2, proteins can be labeled with a rhodamine-based dye described herein. By using protein conjugation reagents known to those skilled in the art, amino acid and peptide conjugates of the invention can be made. In addition, these protein conjugation reagents can be used to label cells and particles such as viruses, as the linkages can be formed to proteins on the cell surface membranes or on viral coats.

The rhodamine-based derivatives and conjugates that are the subject of this invention are based upon the general structure shown by Formula A below:

FORMULA A

In the Formula A structure, $R_1$ and $R_{10}$ taken alone are hydrogen or halogen; $R_2$, $R_5$, $R_6$ and $R_9$ taken alone are hydrogen, alkyl, carboxyalkyl, aminoalkyl, alkylether, alkylthioether, halogen or alkoxy; $R_3$, $R_4$, $R_7$ and $R_8$ taken alone are hydrogen, alkyl, carboxyalkyl, aminoalkyl, cycloalkyl, aryl, or alkyl, cycloalkyl, or aryl substituted so as to have additional functional groups attached, including but not limited to alkoxy, sulfate, phosphate, or nitrate; $R_2$ and $R_3$ taken together are alkyl chains each having from 2 to 5 carbon atoms connecting the 2' carbon to the nitrogen attached to the 3' carbon; $R_9$ and $R_8$ taken together are alkyl chains each having from 2 to 5 carbon atoms connecting the 7' carbon to the nitrogen attached to the 6' carbon; $R_4$ and $R_5$ taken together are alkyl, each having from 2 to 5 carbon atoms connecting the 4' carbon to the nitrogen attached to the 3' carbon; $R_6$ and $R_7$ taken together are alkyl, each having from 2 to 5 carbon atoms connecting the 5' carbon to the nitrogen attached to the 6' carbon; $R_3$ and $R_4$ taken together form an alkyl or alkylene chain containing up to 5 atoms in the principal chain, consisting of carbon and one or more heteroatoms from the group consisting of nitrogen or oxygen, with both terminal valence bonds of said chain being attached to the nitrogen attached to the 3' carbon; $R_7$ and $R_8$ taken together form an alkyl or alkylene chain containing up to 5 atoms in the principal chain, consisting of carbon and one or more heteroatoms from the group consisting of nitrogen or oxygen, with both terminal valence bonds of said chain being attached to the nitrogen attached to the 6' carbon; $R_{11}$, $R_{12}$, $R_{13}$, and $R_{14}$ are each hydrogen or halogen.

Turning to the amide nitrogen substituents of the Formula A structure, $R_a$ is alkyl, carboxyalkyl, aminoalkyl, cycloalkyl aryl, or arylalkyl, and $R_{a'}$ includes a chemically reactive functional group, including but not limited to alcohol, amine, halogen, carboxylate, hydrazine, sulfhydryl, sulfate, phosphate, or nitrate. The size of the $R_a$ substituent can vary considerably, but preferably the $R_a$ has one carbon atom. The chemically reactive functional group included with $R_{a'}$ is used, as will be more fully described and exemplified hereafter, for further derivatization and will be selected from derivatization and conjugation chemistries well known to those skilled in the art. Among suitable functional groups are amines, alcohols, halogens, carboxylates, hydrazines, sulfhydryls, sulfates, phosphates, and nitrates. Typically, the chemically reactive functional group of $R_{a'}$ is chosen so as to react with a reactive site on an organic molecule, which preferably is a biomolecule or is a molecule that is itself bonded to a solid support material such as controlled pore glass or polystyrene resin.

Where the intended biomolecule of the conjugate is a nucleotide, oligonucleotide, or nucleic acid, then the chemically reactive functional group included in $R_{a'}$ is preferably a phosphoramidite. When reacted with a hydroxyl functional group, the phosphoramidite forms a phosphite ester which, in turn, may be oxidized to give a phosphate ester. By phosphoramidite is meant a moiety having the structure of Formula B:

FORMULA B

In Formula B, $L^1$ is cyanoethyl, alkyl, alkenyl, aryl, arylalkyl, or cycloalkyl; $L_2$ and $L_3$ taken separately each represent alkyl, arylalkyl, cycloalkyl, and cycloalkylaryl; $L_1$ and $L_2$ taken together form an alkylene chain containing up to 5 carbon atoms in the principal chain and a total of up to 10 carbon atoms with both terminal valence bonds of said chain being attached to the nitrogen atom to which $L_2$ and $L_3$ are attached; or $L_2$ and $L_3$ taken together with the nitrogen atom to which they are attached form a saturated nitrogen heterocycle which contains one or more heteroatoms from the group consisting of nitrogen, oxygen, or sulfur.

Thus, oligonucleotides may be labeled by reacting fluorophores having phosphoramidite groups with the 5' hydroxyl of an oligonucleotide. The conversion of the 3-position carboxylate of rhodamines to a non-acidic group (i.e. an amide) in preparing the Formula A fluorophores confers greater stability to phosphoramidite derivatives.

Prior art rhodamine phosphoramidites can be made by reacting the 5- or 6-N-hydroxysuccinimidyl ester of rhodamine with an amino alcohol (e.g. ethanol amine, hexanol amine, or the like) in N,N-dimethylformamide (DMF) or like aprotic polar solvent at room temperature to form a 5- or 6-alcohol amide of the rhodamine dye, which is then separated from the reaction mixture by standard means. The alcohol amide of the rhodamine dye is then reacted with an excess of di-(N,N-diisopropylamino) cyanoethylphosphine at room temperature in acetonitrile containing catalytic amounts of tetrazole and diisopropylamine, to form the rhodamine phosphoramidite, which is separated from the reaction mixture. By contrast, rhodamine phosphoramidites of the present invention are made by reacting the Formula A embodiment at the functionality linked through the 3-position carbon. For example, most simply if one uses the N-methyl amino alcohol derivative of rhodamine, one may react the hydroxyl with tetrazole-activated bis (N,N-diisopropylamino) beta-cyanoethyl phosphite (BIS) in dry dichloromethane or acetonitrile under a dry inert atmosphere at room temperature. The resulting rhodamine phosphoramidite embodiment is purified from the reaction mixture for oligonucleotide synthesis.

The inventive rhodamine phosphoramidites are also useful to prepare novel rhodamine-derivatized solid phase supports. Rhodamine-derivatized solid phase supports allow automated synthesis of 3' rhodamine-labeled oligonucleotides.

For a simple example, rhodamine-derivatized solid phase supports of the invention may be made by reacting the N-methyl carboxylic acid derivative of rhodamine with a derivatized solid phase support matrix containing a base-labile ester bond, a branch point with an indicator (DMT or MMT) group, and a terminal amine group in dimethylformamide or other aprotic organic solvent. The rhodamine-derivatized solid phase support is filtered, washed and dried. Dye derivatization content may be determined by trityl cation assay. Suitable supports include controlled pore glass and polystyrene resins with functional groups to which the rhodamine-based dye may be attached.

Detailed descriptions of the procedures for solid phase synthesis by phosphite triester, phosphotriester, and H-phosphonate chemistries are available (e.g. U.S. Pat. Nos. 4,401,796, 4,415,732, and 4,668,777; *Oligonucleotide Synthesis: A Practical Approach*, IRL Press, Washington, D.C., 1984). Preferably, practice of the present invention involves synthesis of rhodamine-labeled oligonucleotides by the phosphite triester approach. Oligonucleotide synthesis is initiated with a nucleoside-derivatized solid support and nucleotides are successively added to a growing chain of nucleotides by reacting nucleoside phosphoramidites with the 5' hydroxyl of the growing chain. In particular, oligonucleotides are labeled at the 5' end by reacting a rhodamine phosphoramidite of the invention with the 5' hydroxyl of the attached oligonucleotide; or oligonucleotides are labeled at the 3' end by reacting nucleoside phosphoramidites to the hydroxyl of the inventive rhodamine-derivatized solid support.

Generally cleavage of the rhodamine-labeled oligonucleotide from the solid phase support and removal of protecting groups attached to the exocyclic amines are effected by treating the rhodamine-labeled oligonucleotide attached to the solid phase support with a cleavage/deprotection reagent (0.1 N to 1.0 N sodium hydroxide) at 4° to 55° C. for 15 min to 18 hours; preferably the rhodamine-labeled oligonucleotide attached to the solid phase support is treated with 0.1 N sodium hydroxide at 55° C. for 2 hours or at room temperature for 12 to 18 hours. After cleavage and deprotection, the labeled or unlabeled oligonucleotides are purified by standard procedures (*Oligonucleotide Synthesis: A Practical Approach*, IRL Press, Washington, D.C., 1984).

Where $R_{a'}$ includes a phosphoramidite group, then the remainder of the substituent may be a chemically inert chain of alkyl, alkylamide, alkylether, polyether or polyamide containing up to 20 atoms, where the atoms are carbon and one or more heteroatoms from the group consisting of nitrogen or oxygen, and containing linking functionalities allowing chemical coupling between the dye and the phosphoramidite portion; preferably such an inert chain is a chain containing 5–10 atoms, where the atoms are carbon and one or more heteroatoms from the group consisting of nitrogen or oxygen. The phosphoramidite itself may contain a branching structure with an indicator protecting group (DMT or MMT) attached by reaction to a hydroxyl function, where DMT is a dimethoxytrityl and MMT is a monomethoxytrityl group.

Returning to Formula A, a number of functional groups other than a phosphoramidite may be selected for inclusion in the $R_{a'}$ substituent, since the selection will depend upon the biomolecule to be conjugated. In general, conjugates of this invention include the Formula A fluorophore that will have been conjugated with a biomolecule through an amide, ester, ether, or thioether linkage.

Thus, where the biomolecule desired to be conjugated is or includes an amino acid, peptide, or protein, then the preferred derivatives for the Formula A fluorophore will include a functional group that reacts with primary amines or sulfhydryl groups. As will be readily understood by persons skilled in the art of protein conjugation, a variety of protein conjugation derivatives may be used to target amino acid reactions. A number of protein conjugation reagents and techniques are, for example, described by Hermanson in *Bioconjugate Techniques*, Academic Press, San Diego, Calif. 1996. Further, since cells and viruses contain proteins on their surface membranes or viral coats, cells or viral particles can be labeled by practicing this invention. An example of a well-known protein conjugation reagent, one suitable functional group for inclusion in the $R_{a'}$ substituent is succinimidyl ester, which readily reacts with primary amines.

In summary, fluorescent conjugates in accordance with this invention may be prepared that have the structure illustrated by Formula 1.

FORMULA 1 where Z includes the conjugated substance which is a peptide, protein, amino acid, nucleotide, oligonucleotide, or nucleic acid. That is, in Formula 1 the fluorophore may be as has been previously described by Formula A, but $R_{a'}$ derivative has been reacted so as to include the conjugated substance.

The following examples serve to illustrate and not to limit the present invention. Unless defined otherwise, all technical and scientific terms used herein have the same meaning as commonly understood by one of ordinary skill in the art to which this invention belongs. The concentrations of reagents, temperatures, and the values of other variable parameters are only to exemplify the invention and are not to be considered limitations thereof. It is recognized that variations in the synthetic methods and reactants are possible that would fall within the scope and intent of this invention.

Table 1 illustrates the structures of the compounds prepared in Examples 1–9.

TABLE 1

Compound 1

Compound 2

Compound 3

Compound 4

TABLE 1-continued

Compound 5

Compound 6

Compound 7

Compound 8

Compound 9

EXAMPLE 1

Preparation of Tetramethylrhodamine N-methylethanolamine Amide (Compound 1):

Tetramethylrhodamine was synthesized, adapting the method described by Hung et al. (1996), using N,N-dimethylaminophenol and phthalic anhydride as starting materials.

Under nitrogen atmosphere 2.00 grams (4.73 mmoles) of tetramethylrhodamine was suspended in 100 ml of dry dichloromethane, followed by addition of 2.30 grams (5.20 mmoles) of benzotriazol-1-yl-oxy-tris(dimethylamino) phosphonium hexafluorophosphate (BOP) and 0.76 ml (9.46 mmoles) N-methylethanolamine. The reaction mixture was stirred at ambient temperature and monitored by thin layer chromatography (TLC) using Kieselgel 60 F254 plates in 2:1:1 chloroform:methanol:acetone containing 2% (v/v) triethylamine. The reacted mixture was extracted sequentially with an equal volume of 5% (w/v) sodium bicarbonate then saturated sodium chloride solution. The organic phase was collected, dried over anhydrous sodium sulfate and evaporated to dryness. The product was purified by chromatography on silica gel with 2:1:1 chloroform:methanol:acetone containing 2% (v/v) triethylamine. Compound 1 was analyzed by MALDI-TOF mass spectrometry, UV/visible spectrophotometry and analytical TLC. In methanol: absorption (excitation) maximum: 548 nm; fluorescence emission maximum: 573 nm.

EXAMPLE 2

Preparation of Rhodamine B N-methylethanolamine Amide (Compound 2):

Under nitrogen atmosphere 1.00 gram (2.09 mmoles) of rhodamine B (Aldrich Chemical Company, Milwaukee, Wis.) was suspended in 25 ml of dry dichloromethane, followed by addition of 1.02 g (2.23 mmoles) of BOP and 0.34 ml (4.18 mmoles) N-methylethanolamine. The reaction mixture was stirred at ambient temperature and monitored by TLC using Kieselgel 60 F254 plates in 2:1:1 chloroform:methanol:acetone. The reacted mixture was extracted sequentially with an equal volume of 5% (w/v) sodium bicarbonate then saturated sodium chloride solution. The organic phase was collected, dried over anhydrous sodium sulfate and evaporated to dryness. The product was purified by chromatography on silica gel with 2:1:1 chloroform:methanol:acetone. Compound 2 was analyzed by MALDI-TOF mass spectrometry, UV/visible spectrophotometry and analytical TLC. In methanol: absorption (excitation) maximum: 560 nm; fluorescence emission maximum: 579 nm.

EXAMPLE 3

Preparation of Rhodamine 101 N-methylethanolamine Amide (Compound 3):

Under nitrogen atmosphere 0.50 gram (1.01 mmoles) of rhodamine 101 (Acros Organics, Pittsburgh, Pa.) was suspended in 50 ml of dry dichloromethane, followed by addition of 0.49 g (1.12 mmoles) of BOP and 0.162 ml (2.02 mmoles) N-methylethanolamine. The reaction mixture was stirred at ambient temperature and monitored by TLC using Kieselgel 60 F254 plates in 2:1:1 chloroform:methanol:acetone. The reacted mixture was extracted sequentially with an equal volume of 5% (w/v) sodium bicarbonate then saturated sodium chloride solution. The organic phase was collected, dried over anhydrous sodium sulfate and evaporated to dryness. The product was used without further purification. Compound 3 was analyzed by MALDI-TOF mass spectrometry, UV/visible spectrophotometry and analytical TLC. In methanol: absorption (excitation) maximum: 582 nm; fluorescence emission maximum: 602 nm.

EXAMPLE 4

Preparation of Tetramethylrhodamine Phosphoramidite (Compound 4):

Preparation of activated bis (N,N-diisopropylamino) beta-cyanoethyl phosphite (BIS) reagent. Tetrazole-activated BIS was prepared by placing 8.5 mg (0.12 mmole) of tetrazole into a dry bottle and capping with a rubber septum. Dry acetonitrile (2.5 ml) was added by injection through the septum cap. The resulting solution was injected with 0.085 ml (0.24 mmole) of BIS and allowed to stand at ambient temperature for 30 minutes.

Preparation of Compound 4. Under a dry nitrogen atmosphere, 1.0 ml of dry acetonitrile was added to 0.10 mg (0.02 mmole) of dried Compound 1 in a septum-capped bottle. Activated BIS (0.17 ml, 0.017 mmole) was injected as small aliquots through the septum cap. The solution was allowed to react for 15 minutes at ambient temperature and a sample was removed for analysis by TLC (Kieselgel 60F254 in 2:1:1 chloroform:methanol:acetone). Additions of activated BIS and analysis of reaction samples were continued at 15 minute intervals until the reaction was judged to be complete. The resulting solution was used directly for synthesis of labeled oligonucleotides.

EXAMPLE 5

Preparation of Rhodamine B Phosphoramidite (Compound 5):

Under a dry nitrogen atmosphere, 1.20 grams (2.24 mmole) of dried Compound 2 was combined with 86.2 mg (1.23 mmole) of tetrazole and dissolved in 25 ml of dry dichloromethane. BIS (0.74 ml, 2.46 mmole) was added and the reaction mixture was stirred at ambient temperature for one hour. Analysis of a sample by TLC (Kieselgel 60 F254 in 10% methanolic chloroform containing 2% triethylamine) confirmed that the reaction was complete. The reaction was quenched and extracted sequentially with equal volumes of 5% sodium bicarbonate followed by saturated sodium chloride. The organic phase was dried over sodium sulfate and evaporated to dryness. The crude product was purified by chromatography on silica gel, eluting with 50:50 dichloromethane:acetone containing 2% triethylamine. Purified Compound 5 was stored in lyophilized form until used for synthesis of labeled oligonucleotides.

EXAMPLE 6

Preparation of Rhodamine 101 Phosphoramidite (Compound 6):

Under a dry nitrogen atmosphere, 0.5 g (0.91 mmole) of dried Compound 3 was combined with 35.2 mg (0.51 mmole) of tetrazole and dissolved in 20 ml of dry acetonitrile. BIS (0.30 ml, 1.01 mmole) was added and the reaction mixture was stirred at ambient temperature for one hour. Analysis of a sample by TLC (Kieselgel 60 F254 in 10% methanolic chloroform containing 2% triethylamine) confirmed that the reaction was complete. The reaction was quenched, extracted twice with an equal volume of petroleum ether, and evaporated to dryness. The resulting product was dissolved in chloroform containing 2% triethylamine and extracted sequentially with equal volumes of 5% sodium bicarbonate then saturated sodium chloride. The organic phase was dried over sodium sulfate and evaporated to dryness. The crude product was purified by chromatography on silica gel, eluting with 50:50 dichloromethane:acetone containing 2% triethylamine. Purified Compound 6 was stored in lyophilized form until used for synthesis of labeled oligonucleotides.

EXAMPLE 7
Preparation of Tetramethylrhodamine-derivatized controlled Pore Glass (CPG) (Compound 7):

Preparation of tetramethylrhodamine N-methylbutyryl ester. Under nitrogen atmosphere 663 mg of BOP was added to a mixture of 424 mg (1 mmole) of tetramethylrhodamine, 12 mg of dimethylaminopyridine, 251 mg of N-methylbutyryl-methylester-HCl in 20 ml of dimethylformamide. Diisopropylethylamine was used to adjust the solution to pH 8.5. The reaction mixture was stirred at ambient temperature and monitored to completion using TLC (Kieselgel 60 F254 in 15% methanolic chloroform). The reacted mixture was evaporated to a syrup and resuspended in 100 ml of dichloromethane. This solution was extracted sequentially with an equal volume of 5% sodium bicarbonate then saturated sodium chloride solution. The organic phase was collected, dried over anhydrous sodium sulfate and evaporated to dryness. The product was purified by chromatography on silica gel with 7% methanolic chloroform to yield 250 mg of pure compound. Tetramethylrhodamine N-methylbutyryl ester was analyzed by MALDI-TOF mass spectrometry, UV/visible spectrophotometry and analytical TLC. In methanol: absorbance (excitation) maximum: 548 nm; fluorescence emission maximum: 572 nm.

Preparation of tetramethylrhodamine N-methylbutyric acid. Tetramethylrhodamine N-methylbutyryl ester (250 mg) was dissolved in 20 ml of methanol and 5 ml of 1 N sodium hydroxide solution was added. The reaction mixture was stirred at ambient temperature and monitored by TLC (Kieselgel 60 F254 in 15% methanolic chloroform). The reaction mixture was evaporated to an oil and dissolved in 200 ml of water. The aqueous phase was washed twice with and equal volume of dichloromethane. The aqueous layer was adjusted to pH 3 to 4 by 6 N hydrochloric acid and extracted with an equal volume of dichloromethane. The organic layer was collected, dried over anhydrous sodium sulfate and evaporated to dryness. The product yield was 254 mg. Tetramethylrhodamine N-methylbutyric acid was used without further purification.

Preparation of tetramethylrhodamine N-methylbutyryl-CPG (Compound 7). To 2 grams of F-moc-3'-amino-modifier-CPG (Peninsula Laboratories, Inc., San Carlos, Calif.), 20% piperidine-dichloromethane was added. The CPG was shaken for 30 minutes at ambient temperature, filtered, and sequentially washed with acetone, methanol and ether. After drying under vacuum for 3 hours, the CPG was added into a mixture of 250 mg of tetramethylrhodamine N-methylbutyric acid, 0.5 ml triethylamine, 0.39 ml of N,N'-diisopropyl carbodiimide and 20 ml of dichloromethane. The reaction mixture was shaken overnight. The CPG was filtered and washed as described above. The dye derivatization content ("loading") of the CPG solid support was determined to be 30 to 40 $\mu$moles/gram by trityl cation assay.

EXAMPLE 8
Preparation of Tetramethylrhodamine-((N-hydroxysuccinimidyl) (4-N-methylamino) butanoate) amide (Compound 8)

Preparation of tetramethylrhodamine-(methyl(4-N-methylamino) butanoate) amide. Under a dry nitrogen atmosphere, 1.0 g (2.58 mmole) of tetramethylrhodamine was combined with 1.26 g (2.63 mmole) of BOP, 0.52 (3.12 mmole) of methyl 4-(N-methylamino)butanoate hydrochloride, 0.87 ml (6.24 mmole) of triethylamine and 100 ml of dry dichloromethane. The reaction was stirred overnight at ambient temperature. Analysis of a sample by TLC in 2:1:1 chloroform:methanol:acetone confirmed the reaction was complete. The reaction mixture was extracted sequentially with an equal volume of 5% (w/v) sodium bicarbonate then saturated sodium chloride. The organic phase was collected, dried over anhydrous sodium sulfate and evaporated to dryness. The product was used without further purification.

Preparation of tetramethylrhodamine-((4-N-methylamino) butanoic acid) amide. A 1.6 g (3.19 mmole) portion of compound tetramethylrhodamine-(methyl(4-N-methylamino)butanoate) amide was dissolved in 30 ml of methanol. A 7.5 ml portion of 1 N sodium hydroxide was added and the reaction stirred overnight at ambient temperature. Analysis of a sample by TLC in 2:1:1 chloroform:methanol:acetone confirmed the reaction was complete. The reaction mixture was evaporated to dryness and diluted with 50 ml of water. The resulting mixture was extracted twice with an equal volume of dichloromethane. The aqueous phase was collected, acidified with 6 N hydrochloric acid and extracted three times with an equal volume of dichloromethane. The organic phase was collected, dried over anhydrous sodium sulfate and evaporated to dryness. The product was used without further purification.

Preparation of tetramethylrhodamine-((N-hydroxysuccinimidyl) (4-N-methylamino) butanoate) amide (Compound 8). Under a dry nitrogen atmosphere, 0.23 g (0.46 mmole) of compound tetramethylrhodamine-((4-N-methylamino) butanoic acid) amide was combined with 0.16 g (0.69 mmole) of disuccinimidyl carbonate, 0.07 ml (0.923 mmole) of dry pyridine and 20 ml of dry dichloromethane. The reaction was stirred overnight at ambient temperature. Analysis of a sample by TLC in 2:1:1 chloroform:methanol:acetone confirmed the reaction was complete. The reaction was evaporated to dryness, dissolved in a minimum amount of dichloromethane and purified by chromatography on a 50 ml silica column eluting with 2:1:1 chloroform:methanol:acetone. In methanol: absorbance (excitation) maximum: 559 nm; fluorescence emission maximum: 578 nm.

EXAMPLE 9
Preparation of Rhodamine B-(N-methylethanolamide)-succinyl-(N-hydroxysuccinimide) (Compound 9)

Preparation of Rhodamine B-(N-methylethanolamine)-succinate. A 0.100 g (0.21 mmole) portion of compound 2 (Rhodamine B-N-methylethanolamine amide) was combined with 0.023 g (0.23 mmole) of succinic anhydride, 5.0 mg (0.04 mmole) of dimethylaminopyridine and 5 ml of dry acetonitrile. The reaction was quenched with an equal volume of 5% sodium bicarbonate, then the acetonitrile was removed by evaporation. The resulting aqueous phase was collected and extracted three times with an equal volume of saturated sodium chloride, dried over anhydrous sodium sulfate and evaporated to dryness. The product was used without further purification.

Preparation of Rhodamine B-(N-methylethanolamine)-succinyl-(N-hydroxysuccinimide) (Compound 9). A 0.118 g (0.221 mmole) portion of compound Rhodamine B-(N-methylethanolamine)-succinate was combined with 23.0 mg (0.23 mmole) of N-hydroxysuccinimide, 48.0 mg (0.23 mmole) of dicyclohexylcarbodiimide and 5 ml of dry dichloromethane. The reaction was stirred at ambient temperature and monitored by TLC in 2:1:1 chloroform:methanol:acetone. The reaction was extracted with an equal volume of saturated sodium chloride. The organic phase was collected, washed with an equal volume of saturated sodium chloride, dried over anhydrous sodium sulfate and evaporated to dryness. The product was used without further purification. In methanol: absorbance (excitation) maximum: 567 nm; fluorescence emission maximum: 586 nm.

EXAMPLE 10
Solid Phase Synthesis of Rhodamine Labeled Oligonucleotides and Cleavage and Deprotection with 0.1 N Sodium Hydroxide Oligonucleotide synthesis was performed using an Eppendorf Ecosyn 300+DNA synthesizer according to manufacturer's instructions. Oligonucleotides were synthesized at a 1 μmole scale. Dye phosphoramidites were reconstituted to a concentration of 100 mg/ml with dry acetonitrile. Labeled oligonucleotides (5 mer to 10 mer lengths) were released from the solid support and deprotected by treating with 0.5 ml of 0.1 N sodium hydroxide for 2 hours at 55° C. Labeled oligonucleotides were purified and analyzed by TLC (Kieselgel 60 F254 in 55:10:35 isopropanol:water:ammonia) or by polyacrylamide gel electrophoresis according to standard procedures (Sambrook et al., *Molecular Cloning: A Laboratory Manual*, 2nd Edition, Cold Spring Harbor Laboratory Press, 1989).

Compounds 5, 7, 4, and 6 were used to label oligonucleotides and FIG. 1 shows data when the inventive embodiments, rhodamine-labeled oligonucleotides, were electrophoresed in a 19% polyacrylamide, 10 M urea, Tris-borate (89 mM Tris-borate, 2 mM EDTA) gel. The gel was illuminated on an ultraviolet light box and fluorescent images were captured using a NucleoVision CCD camera system fitted with a rhodamine filter (NucleoTech, Inc., Foster City, Calif.). Samples loaded in lanes: A) poly-dT 9 mer labeled during synthesis at the 5' end using Compound 5: rhodamine B phosphoramidite; B) poly-dT 10 mer labeled during synthesis at the 3' end using Compound 7: tetramethylrhodamine-derivatized controlled pore glass; C) poly-dT 11 mer labeled during synthesis at the 5' end using Compound 4: tetramethylrhodamine phosphoramidite; D) poly-dT 11 mer labeled during synthesis at the 5' end using Compound 6: rhodamine 101 phosphoramidite.

Table 2 below gives the fluorescence excitation and emission wavelengths of oligonucleotides labeled with three of the inventive rhodamine phosphoramidite embodiments, and of one of the inventive embodiments attached to a solid support (controlled pore glass or CPG).

TABLE 2

| Labeling reagent | Label position | Oligo-nucleotide Synthesized | Excitation Maximum | Emission Maximum |
|---|---|---|---|---|
| Compound 4: tetramethylrhodamine phosphoramidite | 5' end | poly-dT 11 mer | 559 nm | 579 nm |
| Compound 5: rhodamine B phosphoramidite | 5' end | poly-dT 9 mer | 570 nm | 587 nm |
| Compound 6: rhodamine 101 phosphoramidite | 5' end | poly-dT 11 mer | 590 nm | 604 nm |
| Compound 7: tetramethylrhodamine-N-methylbutyryl-CPG | 3' end | poly-dT 10 mer | 565 nm | 582 nm |

All spectral measurements were taken with purified labeled oligonucleotides dissolved in phosphate buffered saline solution, pH 7.2 (JRH Biosciences) using a Shimadzu UV-1601 UV-visible spectrophotometer and a Shimadzu RF-5301PC spectrofluorophotometer.
Note that the excitation and emission maxima of the labeled oligonucleotides are shifted to longer wavelengths relative to the free dye reagent excitation and emission maxima. The red-shift of excitation and emission maxima is also seen with oligonucleotides labeled with prior art 5- or 6-TAMRA by conventional methods.

A derivative such as DMT-5-Dye-deoxyuridine phosphoramidite (DMT-5-dye-dU-CEP) may be used to add a dye-labeled deoxyuridine (dU) residue to an oligonucleotide at the 5' end or any point within the sequence between the 5' and 3' ends during the automated oligosynthesis. Usually, a researcher would substitute the dye-dU for a thymidine (dT) in the sequence so that the hybridization base pairing is not affected.

Additionally used derivatives are dye-deoxynucleotide triphosphate (dye-dNTP), dye-ribonucleotide triphosphate (dye-NTP), and dye-dideoxynucleotide triphosphate (dye-ddNTP) compounds. These reagents are useful to label DNA or RNA by enzymatic incorporation of the dye-linked dNTP or NTP.

The dye-labeled dideoxynucleotide triphosphates (ddNTP) may be incorporated enzymatically into DNA for DNA sequencing applications as a chain terminator in the Sanger dideoxy sequencing method (Sanger et al., *J. Mol. Biol.*, 143, pp. 161–178, 1980). There is prior art for these compounds. Dye-ddATP, dye-ddCTP, dye-ddGTP, dye-ddTTP analogs are also contemplated.

EXAMPLE 11

Labeled proteins with rhodamine succinimidyl ester conjugation reagents (Compounds 8 and 9) are illustrated by FIG. 2. Compounds 8 and 9 were dissolved in anhydrous dimethylsulfoxide (DMSO) to a concentration of approximately 10 mg/ml. The reagent concentration was calculated from the absorption maximum, assuming a molar extinction coefficient of 90,000 in methanol for the rhodamine dye reagents. Bovine serum albumin (BSA) (molecular weight 66,200 Daltons) was dissolved in phosphate buffered saline (PBS) solution (JRH Biosciences, Lenexa, Kans.) to a concentration of 4.16 mg/ml. The protein was reacted with rhodamine succinimidyl ester reagent in a reaction tube containing 0.2 ml of BSA, 20 μl of 1 M sodium bicarbonate, pH 8.3, and an 8- to 15-fold molar excess of labeling reagent (Compound 8 or Compound 9). The conjugation reaction proceeded for about 1 hour at room temperature on a tube shaker. A 6 μl volume of 6 M hydroxylamine, pH 8.5 was added to stop the conjugation reaction. Unincorporated rhodamine reagent was separated from the labeled BSA by gel filtration chromatography on BioGel P6 spin columns (Bio-Rad Laboratories, Hercules, Calif.). Labeled BSA was analyzed by UV/visible spectrophotometry, fluorescence spectrophotometry, and SDS-polyacrylamide gel electrophoresis by standard methods (Sambrook et al., *Molecular Cloning: A Laboratory Manual*, $2^{nd}$ Edition, Cold Spring Harbor Laboratory Press, 1989). For tetramethylrhodamine-conjugated BSA in PBS solution: absorbance (excitation) maximum: 564 nm; fluorescence emission maximum: 581 nm. For Rhodamine B-conjugated BSA in PBS solution: absorbance (excitation) maximum: 569 nm; fluorescence emission maximum: 585 nm.

It is to be understood that while the invention has been described above in conjunction with preferred specific embodiments, the description and examples are intended to illustrate and not limit the scope of the invention, which is defined by the scope of the appended claims.

It is claimed:
1. A fluorophore conjugate comprising:
    a conjugated substance and a fluorophore, the conjugated substance being an amino acid, peptide, protein, nucleotide, oligonucleotide, or nucleic acid to which is attached one or more fluorophores, the fluorophore conjugate having the structure illustrated by Formula 1

FORMULA 1 where $R_1$ and $R_{10}$ taken alone are hydrogen or halogen; $R_2$, $R_5$, $R_6$ and $R_9$ taken alone are hydrogen, alkyl, carboxyalkyl, aminoalkyl, alkylether, alkylthioether, halogen or alkoxy; $R_3$, $R_4$, $R_7$ and $R_8$ taken alone are hydrogen, an alkyl, carboxyalkyl, aminoalkyl, cycloalkyl, or aryl; $R_2$ and $R_3$ taken together are alkyl chains each having from 2 to 5 carbon atoms connecting the 2' carbon to the nitrogen attached to the 3' carbon; $R_9$ and $R_8$ taken together are alkyl chains each having from 2 to 5 carbon atoms connecting the 7' carbon to the nitrogen attached to the 6' carbon; $R_4$ and $R_5$ taken together are alkyl, each having from 2 to 5 carbon atoms connecting the 4' carbon to the nitrogen attached to the 3' carbon; $R_6$ and $R_7$ taken together are alkyl, each having from 2 to 5 carbon atoms connecting the 5' carbon to the nitrogen attached to the 6' carbon; $R_3$ and $R_4$ taken together form an alkyl or alkylene chain containing up to 5 atoms in the principal chain, consisting of carbon and one or more heteroatoms from the group consisting of nitrogen or oxygen, with both terminal valence bonds of said chain being attached to the nitrogen attached to the 3' carbon; $R_7$ and $R_8$ taken together form an alkyl or alkylene chain containing up to 5 atoms in the principal chain, consisting of carbon and one or more heteroatoms from the group consisting of nitrogen or oxygen, with both terminal valence bonds of said chain being attached to the nitrogen attached to the 6' carbon; $R_{11}$, $R_{12}$, $R_{13}$, and $R_{14}$, are each hydrogen or halogen, where $R_8$ is an alkyl, carboxyalkyl, aminoalkyl, cycloalkyl, and aryl, having from 1 to 10 carbon atoms, and Z represents a linker plus the conjugated substance, wherein said conjugated substance lacks a lactam ring.

2. The conjugate as in claim 1 wherein the conjugated substance is bound to the fluorophore through an amide, ester, ether, disulfide, or thioether linkage.

3. The conjugate as in claim 1 wherein the linkage between the fluorophore and conjugated substance has a phosphate ester.

4. The fluorescent conjugate as in claim 1 wherein the conjugated substance is attached to a solid support.

5. The fluorescent conjugate as in claim 4 wherein the solid support is controlled pore glass.

6. The fluorescent conjugate as in claim 4 wherein the solid support is a polymer support.

7. The fluorescent conjugate as in claim 1 wherein the conjugated substance is part of a cell membrane.

8. The fluorescent conjugate as in claim 1 wherein the conjugated substance is part of a viral coat.

9. The fluorescent conjugate as in claim 1 wherein the fluorophore is derived from tetramethylrhodamine.

10. The fluorescent conjugate as in claim 1 wherein the fluorophore is derived from rhodamine 101.

11. The fluorescent conjugate as in claim 1 wherein the fluorophore is derived from rhodamine B.

* * * * *